United States Patent [19]
Estell et al.

[11] Patent Number: 5,155,033
[45] Date of Patent: Oct. 13, 1992

[54] SUBTILISINS MODIFIED AT POSITION 225 RESULTING IN A SHIFT IN CATALYTIC ACTIVITY

[75] Inventors: David A. Estell, San Mateo; Robert M. Caldwell, San Francisco; Richard R. Bott, Burlingame; Thomas P. Graycar, Pacifica, all of Calif.

[73] Assignee: Genencor, Inc., San Francisco, Calif.

[21] Appl. No.: 294,340

[22] Filed: Jan. 6, 1989

[51] Int. Cl.⁵ .......................... C12N 9/54; C12N 9/56; C12N 15/00
[52] U.S. Cl. .................................... 435/221; 435/222; 435/172.1; 935/14
[58] Field of Search ................. 435/221, 222, 220, 10, 435/14

[56] References Cited
U.S. PATENT DOCUMENTS 4,760,025 7/1988 Estell et al. ..................... 435/222

OTHER PUBLICATIONS

Bott et al, "The Three-Dimensional Structure of *Bacillus amyloliquefaciens* Subtilisin . . . ", *J. Biol. Chem.*, vol. 263, No. 16, Jun. 5, 1988, pp. 7895-7906.
McPhalen et al. "Structural Comparison of Two Serine Proteinase-Protein Inhibitor Complexes . . . " Biochemistry, 27:6582-6598, 1988.

*Primary Examiner*—Robert A. Wax
*Assistant Examiner*—Keith D. Hendricks
*Attorney, Agent, or Firm*—Margaret A. Horn

[57] ABSTRACT

There are described certain subtilisins wherein the amino acid sequence of such subtilisins has been modified at a position equivalent to +225 in *Bacillus amyloliquefaciens*, such that an amino acid selected from the group consisting of alanine, leucine, methionine, glutamine, valine, and serine, has been substituted for the amino acid residue naturally occurring at such position.

3 Claims, 7 Drawing Sheets

FIGURE 3a

```
01  A Q S V P Y G V S Q I K A P A L H S Q G Y T G S N V K V A V I D S G I D S S H P  (B.amyloliq.)
    A Q S V P Y G I S Q I K A P A L H S Q G Y T G S N V K V A V I D S G I D S S H P  (B.subtilis)
    A Q T V P Y G I P L I K A D K V Q A Q G F K G A N V K V A V L D T G I Q A S H P  (B.lichen.)
                            10              20              30

```
                                    10              20            30
01  A Q S V * P Y * * * G V S Q I K A P A L H S Q G Y T G S N V K V A V I D S    (B.amylo.)
    Y T P N D P Y F S S R Q Y G P Q K I Q A P Q A W D I A E * G S G A K I A I V D T  (Thermitase)

TOTALLY CONSERVED RESIDUES IN SUBTILISINS

```
1                             10                                    20
. . . . P . . . . . . . . . . . . . . .

21                            30                                    40
. . G . . . . . . D . G . . . . H . . .

41                            50                                    60
. . . . . G . . . . V . . . . . . . . .

61                            70                                    80
. . . H G T H . . G . . . . . . . . . .

81                            90                                   100
. . G . . . . . . . . . . V L . . . . G 101                          110                                   120
S G . . . . . . . G . . . . . . . . . .

121                          130                                   140
. . . . . L G . . . . . . . . . . . . .

141                          150                                   160
. . . . . G . . . . . . G N . . . . . .

161                          170                                   180
. . . . . . Y P . . . . . . . . V . . .

181                          190                                   200
. . . . . . S F S . . . . . . . . . . .

201                          210                                   220
P G . . . . . . . . . . . . . . . . G T 221                          230                                   240
S M A . P H V A G . . . . . . . . . . .

241                          250                                   260
. . . . . . R . . . . . . . . . . . . .

261                          270
. . . . . . . . N . . . . . .
```

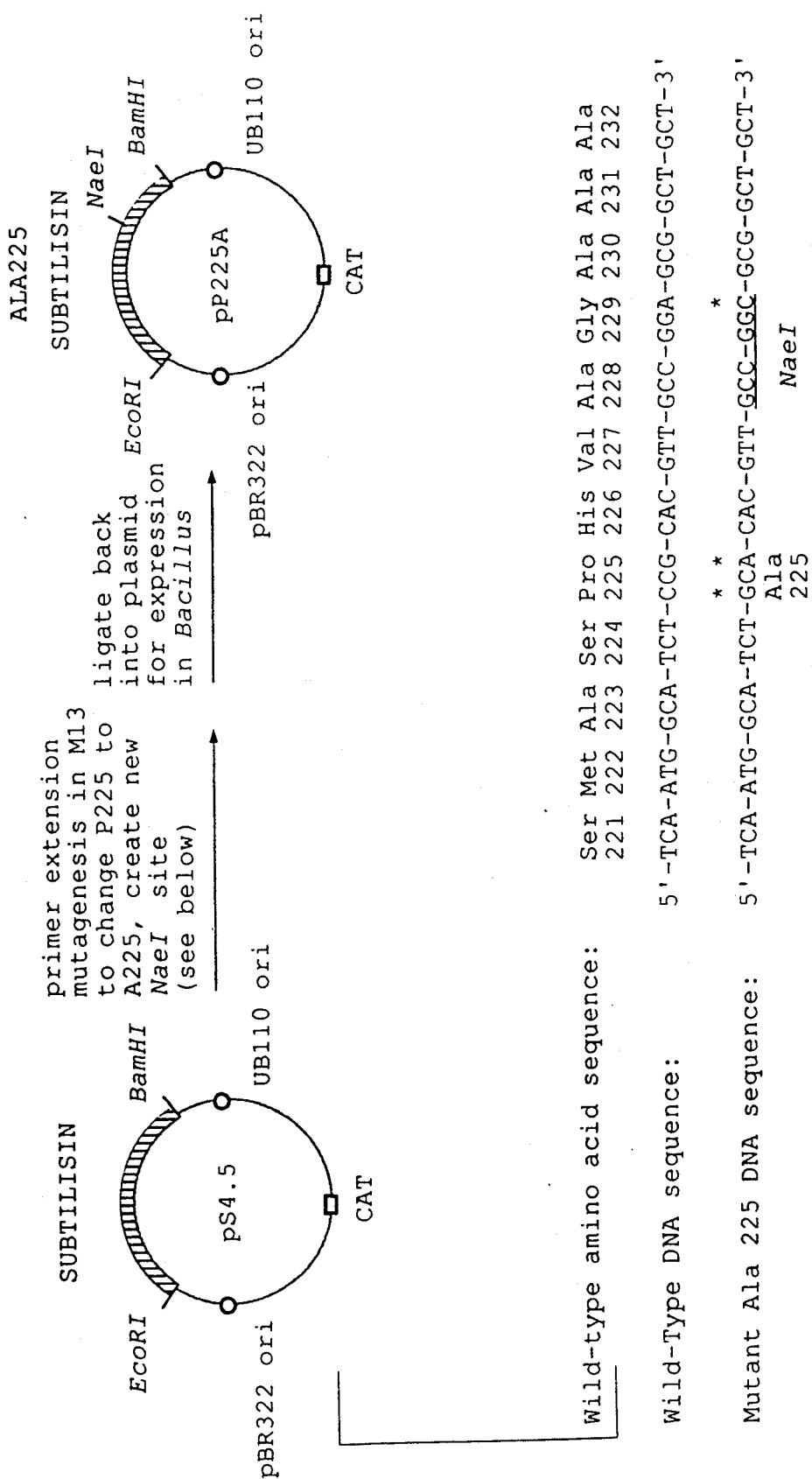

SUBTILISINS MODIFIED AT POSITION 225 RESULTING IN A SHIFT IN CATALYTIC ACTIVITY

Cross-reference is made to U.S. patent application Ser. No. 084,589 filed Aug. 12, 1987 (pending), which is a continuation-in-part of U.S. patent application Ser. No. 035,652 filed Apr. 6, 1987 (abandoned), which is a continuation-in-part of U.S. patent application Ser. No. 858,594 filed Apr. 30, 1986 (abandoned), which is a continuation-in-part of U.S. patent applications Ser. Nos. 614,612 (issued), 614,615 (abandoned), 614,617 (abandoned) and 614,491 (abandoned), all filed May 29, 1984, each of which are incorporated herein by reference. Application Ser. No. 614,612 issued as U.S. Pat. No. 4,760,025 on Jul. 26, 1988.

FIELD OF THE INVENTION

The invention relates to novel carbonyl hydrolase mutants derived from the amino acid sequence of naturally-occurring or recombinant non-human carbonyl hydrolases and to DNA sequences encoding the same. Such mutant carbonyl hydrolases, in general, are obtained by in vitro modification of a precursor DNA sequence encoding the naturally-occurring or recombinant carbonyl hydrolase to encode the substitution, insertion or deletion of one or more amino acids in a precursor amino acid sequence.

BACKGROUND OF THE INVENTION

Serine proteases are a subgroup of carbonyl hydrolase. They comprise a diverse class of enzymes having a wide range of specificities and biological functions. Stroud, R. M. (1974) *Sci Amer.* 131, 74–88. Despite their functional diversity, the catalytic machinery of serine proteases has been approached by at least two genetically distinct families of enzymes: the Bacillus subtilisin-type serine proteases and the mammalian and homologous bacterial trypsin-type serine proteases (e.g., trypsin and *S. gresius* trypsin). These two families of serine proteases show remarkably similar mechanisms of catalysis. Kraut, J. (1977) *Ann. Rev. Biochem.* 46, 331–358. Furthermore, although the primary structure is unrelated, the tertiary structure of these two enzyme families bring together a conserved catalytic triad of amino acids consisting of serine, histidine and aspartate.

In subtilisin-type serine proteases, the OG group of the catalytic side chain of serine (serine-221 in subtilisin) is located near amino terminus of a long central α-helix which extends through the molecule. Bott, et al. (1988) *J. Biol. Chem.* 263, 7895–7906. In *Bacillus amyloliquifaciens* subtilisin this α-helix comprises alanine 223 through lysine 237. This helix is conserved in evolutionarily related subtilisin-type serine proteases but is not found in the catalytic sites of trypsin-type serine proteases.

McPhelan, et al. (1988) *Biochemistry* 27, 6582–6598. The α-helix associated with the active site of subtilisin-type serine proteases has led to the suggestion that the dipole of this helix may have a functional role in catalysis. Hol, W. G. J. (1985) *Prog. Boiphys. Molec. Biol.* 45, 149–195. The lack of α-helix at the active site of the trypsin-type serine proteases, however, has raised the unresolved question of whether the active site helix of subtilisin-type serine proteases is of any significance in catalysis. Hol (1985) supra.

Subtilisin is a serine endoprotease (MW27,500) which is secreted in large amounts from a wide variety of Bacillus species. The protein sequence of subtilisin has been determined from at least four different species of Bacillus. Markland, F. S., et al. (1971) in *The Enzymes*, ed. Boyer, P. D., Acad Press, New York, Vol. III, pp. 561–608; Nedkov, P. et al. (1983) *Hoppe-Seyler's Z. Physiol. Chem.* 364, 1537–1540. The three-dimensional crystallographic structure of subtilisin BPN' (from *B. amyloliquefaciens*) to 2.5 Å resolution has also been reported. Bott (1988) supra: McPhelan (1988) supra: Wright, C. S., et al. (1969) *Nature* 221, 235–242; Drenth, J. et al. (1972) *Eur. J. Biochem.* 26, 177–181. These studies indicate that although subtilisin is genetically unrelated to the mammalian serine proteases, it has a similar active site structure. The x-ray crystal structures of subtilisin containing covalently bound peptide inhibitors (Robertus, J. D., et al. (1972) *Biochemistry* 2439–2449), product complexes (Robertus, J. D., et al. (1972) *Biochemistry* 11, 4293–4303), and transition state analogs (Matthews, D. A., et al (1975) *J. Biol. Chem.* 250, 7120–7126; Poulos, T. L., et al. (1976) *J. Biol. Chem.* 251, 1097–1103), which have been reported have also provided information regarding the active site and putative substrate binding cleft of subtilisin. In addition, a large number of kinetic and chemical modification studies have been reported for subtilisin (Philipp, M., et al. (1983) *Mol. Cell. Biochem.* 51, 5–32; Svendsen, I. B. (1976) *Carlsberg Res. Comm.* 41, 237–291; Markland, F. S. Id.). In one report the side chain of methione at residue 222 of subtilisin was converted by hydrogen peroxide to methionine-sulfoxide (Stauffer, D. C., et al. (1965) *J. Biol. Chem.* 244, 5333–5338). In another, subtilisin was chemically modified to thiosubtilisin (Polgar, L. et al (1981) *Biochem. Biophys. Acta.* 667, 351–354). Based on the analysis of peptide fragments, the authors suggest that the chemical modification of subtilisin to thiosubtilisin caused the modification of serine at position 221 to cysteine.

Substrate specificity is a ubiquitous feature of biological macromolecule that is determined by chemical forces including hydrogen bonding, electrostatic, hydrophobic and stearic interactions. Jencks, W. P., in *Catalysis in Chemistry and Enzymology* (McGraw-Hill, 1969) pp. 321–436; Fersht, A., in *Enzyme Structure and Mechanism* (Freeman, San Francisco, 1977) pp. 226–287. Substrate specificity studies of enzymes, however, have been limited to the traditional means of probing the relative importance of these binding forces. Although substrate analogs can be synthesized chemically, the production of modified enzyme analogs has been limited to chemically modified enzyme derivatives (Kaiser, E. T., et al. (1985) *Ann. Rev. Biochem.* 54, 565–595 and naturally occurring or induced mutants (Kraut, J. (1977) *Ann. Rev. Biochem.* 46, 331–358; Paterson, A. et al. (1979) *J. Gen. Micro.* 114, 65–85; Uehara, H. et al. (1979) *J. Bacteriology* 139, 583–590; Kerjan, P. et al. (1979) *Eur. J. Biochem.* 98, 353–362).

The recent development of various in vitro techniques to manipulate the DNA sequences encoding naturally-occurring polypeptides as well as recent developments in the chemical synthesis of relatively short sequences of single and double stranded DNA has resulted in the speculation that such techniques can be used to modify enzymes to improve some functional property in a predictable way. Ulmer, K. M. (1983) *Science* 219, 666–671. The only working example disclosed therein, however, is the substitution of a single amino acid within the active site of tyrosyl-tRNA synthetase (Cys35Ser) which lead to a reduction in enzymatic activity. See Winter, G., et al. (1982) *Nature* 299, 756-758; and Wilkinson, A. J., et al. (1983) *Biochemistry* 22, 3581-3586 (Cys35Gly mutation also resulted in decreased activity).

When the same t-RNA synthetase was modified by substituting a different amino acid residue within the active site with two different amino acids, one of the mutants (Thr51Ala) reportedly demonstrated a predicted moderate increase in kcat/Km whereas a second mutant (Thr51Pro) demonstrated a massive increase in kcat/Km which could not be explained with certainty. Wilkinson, A. H., et al. (1984) *Nature* 307, 187-188.

Another reported example of a single substitution of an amino acid residue is the substitution of cysteine for isoleucine at the third residue of T4 lysozyme. Perry, L. J., et al. (1984) *Science* 226, 555-557. The resultant mutant lysozyme was mildly oxidized to form a disulfide bond between the new cysteine residue at position 3 and the native cysteine at position 97. This cross-linked mutant was initially described by the author as being enzymatically identical to, but more thermally stable than, the wild type enzyme. However, in a "Note Added in Proof", the authors indicated that the enhanced stability observed was probably due to a chemical modification of cysteine at residue 54 since the mutant lysozyme with a free thiol at Cys54 has a thermal stability identical to the wild type lysozyme.

Similarly, a modified dehydrofolate reductase from *E. coli* has been reported to be modified by similar methods to introduce a cysteine which could be crosslinked with a naturally-occurring cysteine in the reductase. Villafranca, D. E., et al. (1983) *Science* 222, 782-788. The authors indicates that this mutant is fully reactive in the reduced state but has significantly diminished activity in the oxidized state. In addition, two other substitutions of specific amino acid residues are reported which resulted in mutants which had diminished or no activity.

As set forth below, several laboratories have also reported the use of site directed mutagenesis to produce the mutation of more than one amino acid residue within a polypeptide.

The amino-terminal region of the signal peptide of the prolipoprotein of the *E. coli* outer membrane was stated to be altered by the substitution or deletion of residues 2 and 3 to produce a charge change in that region of the polypeptide. Inoyye, S., et al. (1982) *Proc. Nat. Acad. Sci. USA* 79, 3438-3441. The same laboratory also reported the substitution and deletion of amino acid residues 9 and 14 to determine the effects of such substitution on the hydrophobic region of the same signal sequence. Inouye, S., et al. (1984) *J. Biol. Chem.* 259, 3729-3733. In the case of mutants at residues 2 and 3 the authors state that the results obtained were consistent with the proposed loop model for explaining the functions of the signal sequence. However, as reported the mutations at residues 9 and 14 produced results indicating that the signal peptide has unexpended flexibility in terms of the relationship between its primary structure and function in protein secretion.

Double mutants in the active site of tyrosyl-t-RNA synthetase have also been reported. Carter, P. J., et al. (1984) *Cell* 38, 835-840. In this report, the improved affinity of the previously described Thr51Pro mutant for ATP was probed by producing a second mutation in the active site of the enzyme. One of the double mutants, Gly35/Pro51, reportedly demonstrated an unexpected result in that it bound ATP in the transition state better than was expected from the two single mutants. Moreover, the author warns, at least for one double mutant, that it is not readily predictable how one substitution alters the effect caused by the other substitution and that care must be taken in interpreting such substitutions.

A mutant is disclosed in U.S. Pat. No. 4,532,207, wherein a polyarginine tail was attached to the C-terminal residue of $\beta$-urogastrone by modifying the DNA sequence encoding the polypeptide. As disclosed, the polyarginine tail changed the electrophoretic mobility of the urogastrone-polyaginine hybrid permitting selective purification. The polyarginine was subsequently removed, according to the patentee, by a polyarginine specific exopeptidase to produce the purified urogastrone. Properly construed, this reference discloses hybrid polypeptides which do not constitute mutant polypeptides containing the substitution, insertion or deletion of one or more amino acids of a naturally occurring polypeptide.

Single and double mutants of rat pancreatic trypsin have also been reported. Craik, C. S., et al. (1985) *Science* 228, 291-297. As reported, glycine residues at positions 216 and 226 were replaced with alanine residues to produce three trypsin mutants (two single mutants and one double mutant). In the case of the single mutants, the authors stated expectation was to observe a differential effect on Km. They instead reported a change in specificity (kcat/Km) which was primarily the result of a decrease in kcat. In contrast, the double mutant reportedly demonstrated a differential increase in Km for lysyl and arginyl substrates as compared to wild type trypsin but had virtually no catalytic activity.

U.S. Pat. No. 4,760,025 discloses subtilisin mutants wherein a different amino acid is substituted for the naturally-occurring amino acid residues of *Bacillus amyloliquifaciens* subtilisin at positions +32, +155, +104, +222, +166, +64, +33, +169, +189, +217, or +156.

The references discussed above are provided solely for their disclosure prior to the filing date of the instant case, and nothing herein is to be construed as an admission that the inventors are not entitled to antedate such disclosure by virtue of prior invention or priority based on earlier filed applications.

Based on the above references, however, it is apparent that the modification of the amino acid sequence of wild type enzymes often results in the decrease or destruction of biological activity. Moreover, these references do not address the mutation of the particular carbonyl hydrolases disclose herein.

Accordingly, it is an object herein to provide carbonyl hydrolase mutants which have at least one property which is different from the same property of the carbonyl hydrolase precursor from which the amino acid of said mutant is derived.

It is a further object to provide mutant DNA sequences encoding such carbonyl hydrolase mutants as well as expression vectors containing such mutant DNA sequences.

Still further, another object of the present invention is to provide host cells transformed with such vectors as well as host cells which are capable of expressing such mutants either intracellularly or extracellularly.

SUMMARY OF THE INVENTION

The invention includes subtilisin-type carbonyl hydrolase mutants having a different kcat, Km, and/or kcat/Km for various substrates as compared to the precursor carbonyl hydrolase from which the mutant is derived. Such mutants consequently have a different reactivity with or specificity for such substrates. The subtilisin-type carbonyl hydrolase mutants of the invention have an amino acid sequence not found in nature which is derived by the predetermined replacement of at least one amino acid residue of a precursor carbonyl hydrolase with a different amino acid. The mutant enzyme thus obtained is characterized by a shift in catalytic activity for at least one of two different substrates as compared to the precursor enzyme.

The amino acid residue which is substituted in subtilisin comprises proline 225 of the amino acid sequence of *Bacillus amylolicuefaciens* subtilisin and amino acid residues equivalent to said residue in other precursor subtilisin-type carbonyl hydrolases. Such other subtilisin-type carbonyl hydrolases include subtilisin from sources such as *Bacillus subtilis* and *Bacillus licheniformis*, each of which contain proline at position 225. However, as will be described in more detail hereinafter, other subtilisin-type carbonyl hydrolases having functionally or structurally equivalent residues to proline 225 in subtilisin are within the scope of the invention. Such substitutions may be combined with the substitution, insertion or deletion of other amino acid residues as described in U.S. Pat. No. 4,760,025 and the above cross-referenced co-pending applications.

The invention also includes mutant DNA sequences encoding such carbonyl hydrolase mutants. These mutant DNA sequences are derived from a precursor DNA sequence which encodes a naturally occurring or recombinant precursor carbonyl hydrolase. The mutant DNA sequence is derived by modifying the precursor DNA sequence to encode the substitution of one amino acid encoded by the precursor DNA sequence. These recombinant DNA sequences encode mutants having an amino acid sequence which does not exist in nature and at least one property which is substantially different from the same property of the precursor carbonyl hydrolase encoded by the precursor DNA sequence.

Further the invention includes expression vectors containing such mutant DNA sequences as well as host cells transformed with such vectors which are capable of expressing said carbonyl hydrolase mutants.

BRIEF DESCRIPTION OF THE DRAWINGS

FIG. 3A comprises the amino acid sequence for subtilisin form *Bacillus amyloliquefaciens, Bacillus subtilis* varI168 and *Bacillus licheniformis*.

FIG. 3B is a comparison of amino acid sequence of subtilisin from B-amyloliquefaciens and thermitase.

FIG. 3C identifies the conserved residues in subtilisin.

FIG. 4 depicts the construction of mutants at position 225 in subtilisin.

DETAILED DESCRIPTION OF THE INVENTION

Figure 1:
FIG. 1 shows the tertiary structure of subtilisin from *Bacillus amyloliquefaciens* subtilisin.

The inventors have discovered that in vitro mutations at position 225 or equivalent amino acid residues of the non-human carbonyl hydrolase subtilisin alter the catalytic activity, kcat, of the mutant enzyme for a target substrate as compared to the precursor enzyme from which it is derived, i.e. derived by the predetermined substitution of a different amino acid for that in the precursor enzyme at position 225. The mutant carbonyl hydrolases also may have a different Km and kcat/Km ratio and hence altered substrate specificity.

Non-human carbonyl hydrolases, recombinant carbonyl hydrolases, subtilisins, recombinant subtilisins, carbonyl hydrolase mutant, equivalent amino acid residues, prosequence, signal sequence, prepro, expression vector, host cells, operably linked, cassette mutagenesis substrate specificity, multiple mutants and mutants at various other amino acid residues are described in detail in application, Ser. No. 035,652 filed Apr. 6, 1987, and such definitions are incorporated herein by reference.

A change in substrate specificity is defined as a difference between the kcat/Km ratio for the precursor carbonyl hydrolase and that of the hydrolase mutant. The kcat/Km ratio is a measure of catalytic efficiency. Generally, the objective will be to secure a mutant having a greater (numerically large) kcat/Km ratio for a given substrate, thereby enabling the use of the enzyme to more efficiently act on a target substrate. A substantial change in kcat/Km ratio is preferably at least a 2-fold increase or decrease. However, smaller increases or decreases in the ratio (e.g., at least 1.5-fold) are also considered substantial. An increase in kcat/Km ratio for one substrate may be accompanied by a reduction in kcat/Km ratio for another substrate. This is a shift in substrate specificity, and mutants exhibiting such shifts have utility where the precursor hydrolase is undesirable, e.g. to prevent undesired hydrolysis of a particular substrate in an admixture of substrates. Km and kcat are measured in accord with known procedures, as described in EPO Publication No. 0130756 or as described herein.

A change in catalytic activity is defined as a difference between the kcat of the precursor carbonyl hydrolase for a particular target substrate as compared to that of the mutant carbonyl hydrolase for the same substrate. Generally, mutants having a greater (numerically larger) kcat for the target substrate are desired. Such mutants will have a greater catalytic activity with such substrates and consequently will preferentially react with such substrates compared to the precursor enzyme A substantial change in kcat is preferably at least a two-fold increase in kcat. However, smaller increases such as a 1.5-fold increase in kcat are significant provided the numerical value of kcat is relatively large. Thus, a change in kcat from 500/sec to 750/sec is a substantial change. A change from 5/sec to 7.5/sec, for example, is not necessarily a substantial change in kcat.

A shift in catalytic activity is defined as the difference between the kcat ratio for two different substrates for the precursor carbonyl hydrolase as compared to the mutant carbonyl hydrolase. Thus, for example, the mutant subtilisin disclosed herein containing the substitution of alanine for proline at position 225 has a shift in catalytic activity, as compared to subtilisin not modified at position 225, for ester and anilide substrates. A shift in catalytic activity is generally measured by determining the ratio of kcat for the precursor carbonyl hydrolase for two different substrates. The kcat ratio is also determined for the carbonyl hydrolase mutant. The kcat ratios for the precursor and mutant enzymes are then compared. A substantial change in kcat substrate ratio is preferably at least a five-fold increase or decrease in the kcat substrate ratio of the mutant enzymes as compared to that of the precursor enzyme. However, smaller increases or decreases in the kcat substrate ratio (e.g. at least about two-fold) are also considered substantial.

Figure 2:
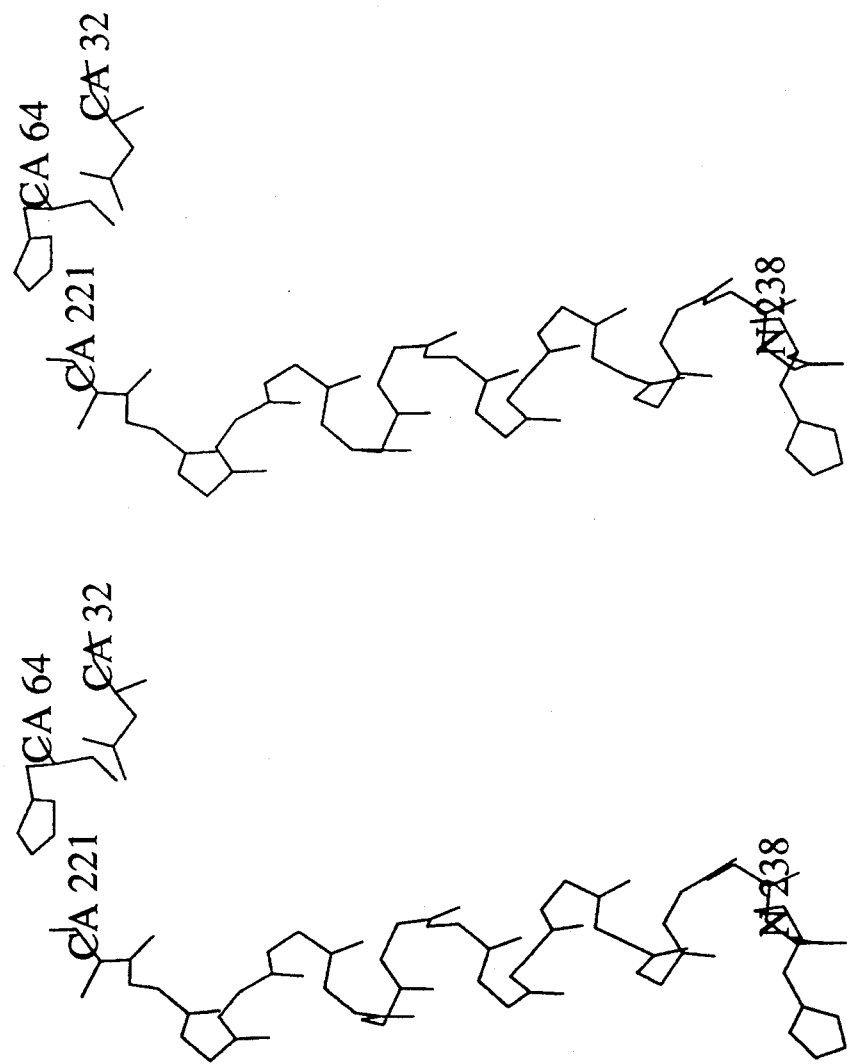
FIG. 2 is a stereo view of the α-helix associated with the catalytic Ser221 in subtilisin.

The three-dimensional structures of related subtilisins show a number of highly conserved structural features. The catalytic serine, Ser221, is found near the beginning of a helix extending through the molecule, the sequence of which is conserved in evolutionarily related subtilisin-type serine proteases. FIG. 1 shows the three dimensional x-ray structure of subtilisin from *Bacillus amyloliquefaciens*. The high-lighted segment comprises amino acid residues serine 221 through lysine 237. A stereo view of this segment isolated from the remainder of the molecule is shown in FIG. 2. There is a discontinuity at the junction of the $3_{10}$ helix 219-222 and α-helix 223-237 which is a direct consequence of the presence of proline at position 225. The carbonyl oxygens of residues 221 and 222 form hydrogen bonds with sidechain atoms rather than the amide nitrogens of residues 225 and 226 respectively. One of these hydrogen bonds, between the carbonyl oxygen of Ser222 and the OG of Ser225, is in turn part of an extensive hydrogen bonding network. Bott (1988) supra. Proline is considered a strong helix breaker because it prevents the formation of a hydrogen bond between the carbonyl oxygen of the residue n-4 from the proline, in this case Ser221 and the nitrogen of proline 225. This results in the kink in the helix.

Figure 3A:
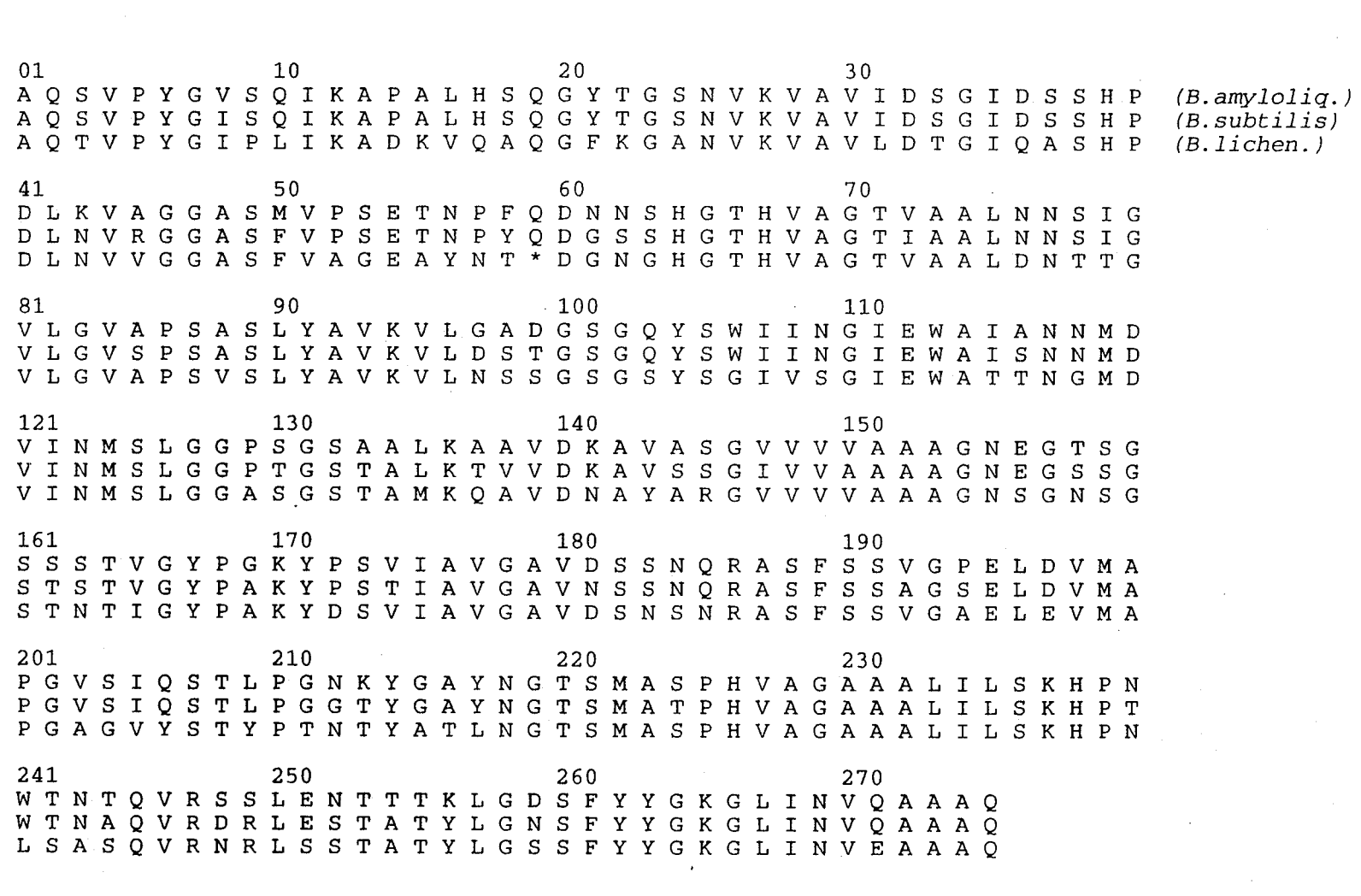
Figure 3B:
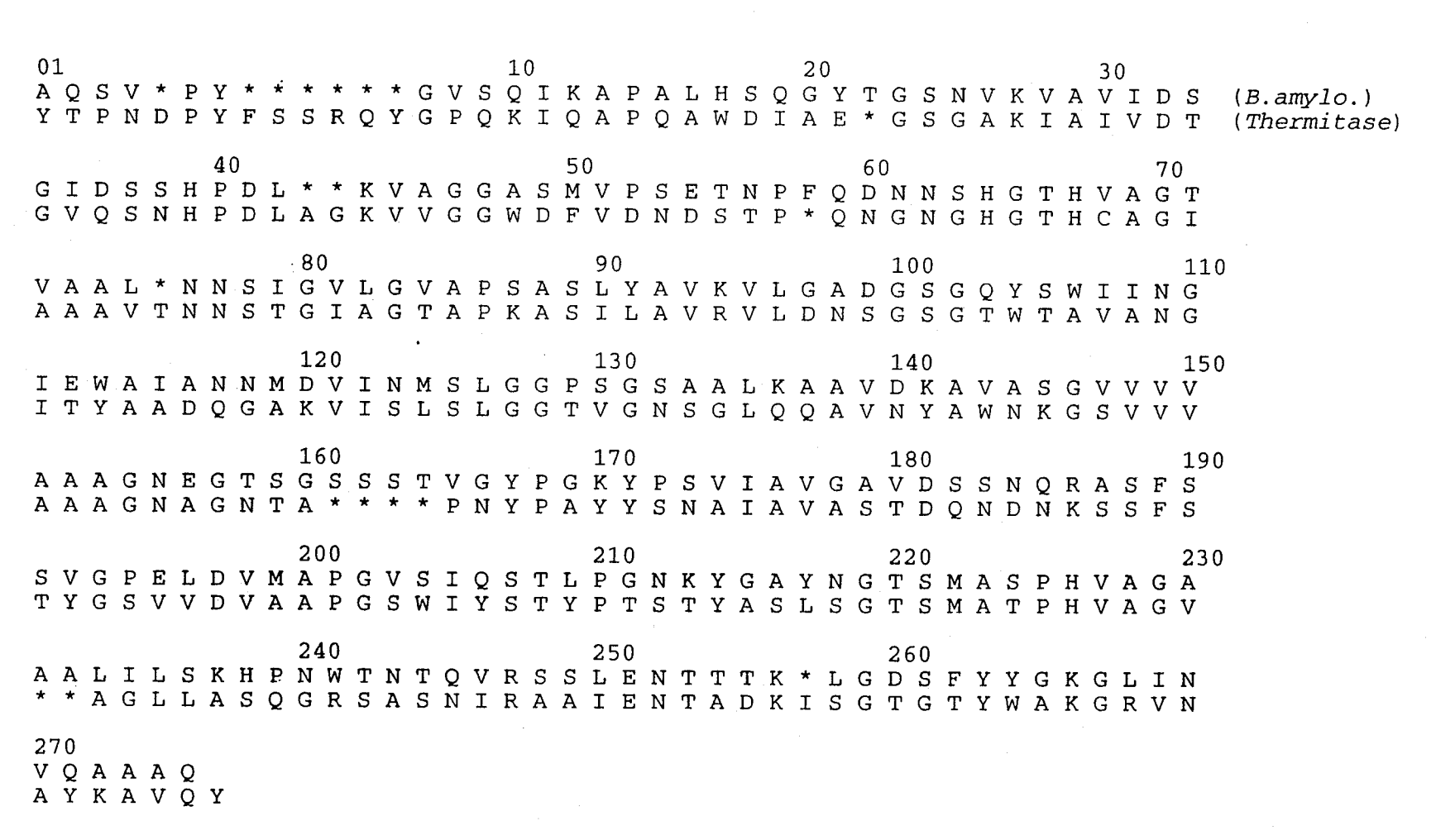

The conserved nature of this kink is further exemplified by the amino acid sequence of various subtilisins. FIGS. 3A and 3B show the sequence homology of subtilisins obtained from *Bacillus amylolicuefaciens* *Bacillus subtilis* varI 168, *Bacillus licheniformis* and thermitase. FIG. 3C identifies the various residues among the subtilisins which are conserved. As can be seen, the residues between gly219 and gly229 are totally conserved except for the residues at position 224. Thus, the modifications described herein for subtilisin from *Bacillus amyloliquefaciens* are expected to produce similar results for other carbonyl hydrolases of the subtilisin-type. Such subtilisin-like carbonyl hydrolases accordingly are defined as any carbonyl hydrolase having a catalytic amino acid residue structurally or functionally equivalent to the serine 221 in *Bacillus amyloliquefaciens* subtilisin which is located at the terminus of a α-helix. Examples of such subtilisin-type carbonyl hydrolases include subtilisin from *Bacillus subtilis*, *Bacillus licheniformis*, thermitase from *Thermoretinomyces valgaris* and Proteinase K from fungi (*Tritirachium album limber*).

As disclosed herein, the substitution of proline 225 with alanine produces a shift in catalytic activity of the mutant enzyme for ester containing substrates as compared to anilide substrates which are closely related to amide bonds. This residue is dispensable for the kink preceding the α-helix (residues 223-237). This single substitution causes a shift in catalytic activity toward ester substrates verses anilide substrates of almost 30-fold as compared to naturally occurring subtilisin. It also results in a partial elimination of the kink so that the α-helix extends from residue 221-237. Modifications of this position with other amino acids are also expected to produce mutant enzymes demonstrating a shift in catalytic activity for different substrates and similar structural consequences. Thus, other amino acids other than alanine may be used to replace the proline at position 225. Such amino acids preferably include leucine, methionine, glutamine, valine and serine, most preferably serine and leucine. These amino acids are expected to extend the α-helix removing the discontinuity, or kink, in a manner analogous to the alanine substitution. Mutant enzymes containing such substituted amino acids at position 225 are also expected to demonstrate a shift in catalytic activity towards ester substrates as compared to anilide or amide substrates.

Construction and Characterization of a Position 225 Mutant

The procedure used to substitute alanine for proline at position 225 in the *Bacillus amyloliquefaciens* subtilisin gene is illustrated generally in FIG. 4. Primer extension mutagenesis on a single stranded M13 subclone using the mutagenic oligonucleotide in FIG. 4 was employed. Plasmid pPro225A was used to transform *E-coli* MM294.

Clones from this transformation were used to transform *B. subtilis* and transformants were plated on Luria agar containing skim milk in order to detect protease secretion. One protease secreting transformant was selected for enzyme purification and characterization and for sequence analysis to ensure that the coding sequences in and around the cassette were correct.

Amino acid substitutions at position 225 alter the enzymes esterase/amidase activity. Table I compares the ratio of ester and anilide substrate kcat values for wild-type enzyme and subtilisin having the amino acid proline replaced with alanine at position 225. Measurements were performed using the substrates succinyl-Ala-Ala-Pro-Phe-p-nitroanilade and succinyl-Ala-Ala-Pro-Phe-thiobenzyl ester at pH 8.6, 25 degrees Celsius.

TABLE I

| Enzyme | kcat ester substrate/ kcat anilide substrate |
|---|---|
| Wild-type | 33 |
| Ala-225 | 960 |

In addition, Km was determined for these two substrates for subtilisin and the mutant containing the alanine substitution. The results of that determination together with a calculation of kcat/Km is summarized in Table II.

TABLE II

| Name | Substrate | pH | kcat | Km | kcat/Km |
|---|---|---|---|---|---|
| B.a.Subt | sAAPFpNA | 8.60 | 50. | 1.40 e-4 | 3.57 e5 |
| B.a.Subt | sAAPFsbz | 8.60 | 1650. | 6.80 e-5 | 2.43 e7 |
| A225 | sAAPFpNA | 8.60 | 3.6 | 6.20 e-4 | 5.75 e3 |
| A225 | sAAPFsbz | 8.60 | 3420. | 3.99 e-4 | 8.57 e6 |

One of the most striking structural features of subtilisins is a long helix extending through the molecule comprising amino acids 221 through 238. The first turn of this helix is interrupted by Pro 225 which causes a kink between the $3_{10}$ helix 219-222 and the o-helix 223-237.

An increase in the effective dipole of the α-helix would increase the electrophilicity of the oxyanion hole. The amide nitrogen of Ser221 along with the $n_\delta 2$ of Asn155 form the oxyanion hole. An increase of dipole strength would be expected by replacing Pro225 with alanine to allow hydrogen bond formation between Ser221 and the amide nitrogen of alanine 225 thereby eliminating the kink in the α-helix. Increasing the dipole in the α-helix would increase the electrophilicity of the amide nitrogen of Ser221. Based on the expected increase in electrophilicity, the catalytic efficiency of the mutant enzyme for amide substrates should be increased.

As can be seen, however, the substitution of proline for alanine resulted in just the opposite. The rate of peptide bond hydrolysis actually decreased (see kinetic data). The helix dipole therefore does not appear to be important for amidolysis. The rate of ester hydrolysis, however, increased for the Pro 225A mutant as compared to the wild-type subtilisin.

Figure 5A:
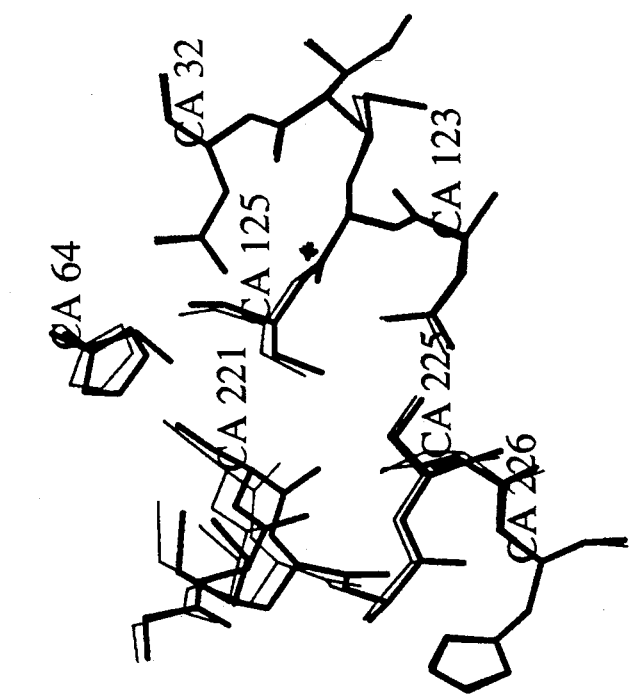
FIG. 5A and 5B are a stereo view of residues 220 through 230 of wild type and Pro 225A subtilisin, respectively.
Figure 5B:
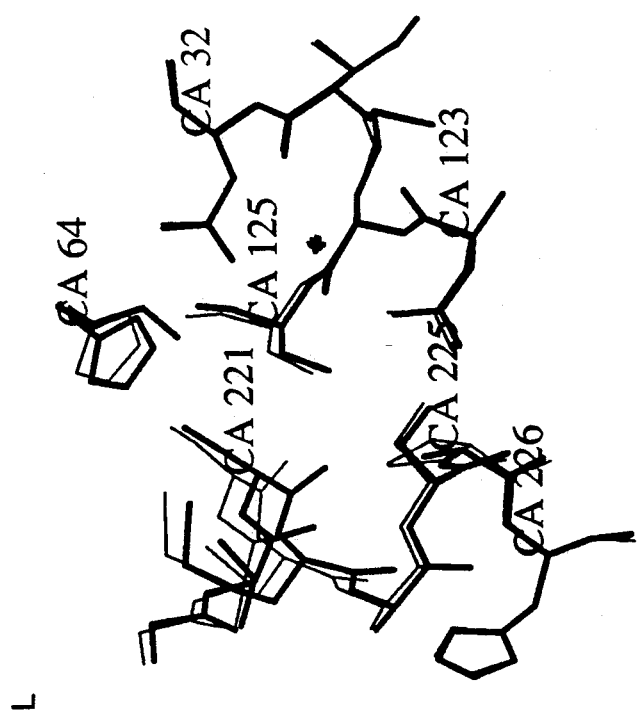

FIG. 5 shows the difference in local structure between wild-type (Pro225) and mutant (Ala225) enzymes. As can be seen, the helix in the Ala225 mutant extends from 221 rather than 223. The removal of the kink essentially adds an additional turn of α-helix comprising residues 221 through 224. Having described the preferred embodiments of the present invention, it will appear to those ordinarily skilled in the art that various modifications may be made to the disclosed embodiments, and that such modifications are intended to be within the scope of the present invention.

What is claimed is:

1. An essentially pure subtilisin wherein the amino acid residue equivalent to position +225 of *Bacillus amyloliquifaciens* subtilisin as shown in FIG. 3A, has been replaced with a different naturally occurring amino acid selected from the group consisting of alanine, leucine, methionine, glutamine, valine, and serine, wherein the resulting mutated subtilisin is characterized by a shift in catalytic activity of at least 1.5 fold, for at least one of two different substrates as compared to a subtilisin wherein the position +225 residue is the same as that which is naturally occurring for said subtilisin.

2. A subtilisin of claim 1 wherein the resulting mutated subtilisin is characterized by a shift in catalytic activity for ester substrates as compared to anilide substrates.

3. The subtilisin of claim 1 wherein said replacement comprises Pro225Ala.

* * * * *